United States Patent [19]
Ashcroft et al.

[11] 4,335,960
[45] Jun. 22, 1982

[54] APPARATUS FOR DETECTING THE PRESENCE OF SURFACE IRREGULARITIES IN ARTICLES MADE OF TRANSPARENT MATERIAL

[75] Inventors: Richard I. Ashcroft, Harpenden; David Kaktovics, Gainsborough, both of England

[73] Assignee: United Glass Limited, Middlesex, England

[21] Appl. No.: 151,619

[22] Filed: May 20, 1980

[30] Foreign Application Priority Data

May 21, 1979 [GB] United Kingdom ................. 7917540

[51] Int. Cl.³ ............................................. G01N 21/01
[52] U.S. Cl. ................................. 356/240; 250/223 B
[58] Field of Search ............... 356/237, 239, 240, 244; 250/223 B; 209/524, 526

[56] References Cited
U.S. PATENT DOCUMENTS 3,356,853  12/1967  Rottmann ............................ 356/240
3,770,969  11/1973  Ansevin et al. ................. 356/240 X
3,887,284   6/1975  Gender et al. ....................... 356/240
4,221,867   9/1980  McFadden ...................... 356/244 X

FOREIGN PATENT DOCUMENTS 1213145  11/1970  United Kingdom ................ 356/239

Primary Examiner—Vincent P. McGraw
Attorney, Agent, or Firm—Cushman, Darby & Cushman

[57] ABSTRACT

Apparatus for detecting the presence of surface irregularities in transparent articles, especially spikes on the inside base of glass containers.

The containers (5) are passed rotatably over a slit (7) having an opaque line (11) situated centrally about the longitudinal axis of the slit. A pair of light sources (15) are positioned beneath the slit and to either side of the opaque line (11) so that, in the absence of surface irregularities, light is refracted at an oblique angle through the container base. A diode-array camera (13) situated vertically above the slit and focussed thereon normally receives no light from the light sources. In the presence of a defect, diffraction of light occurs into the area of view of the camera causing a "defect present" signal to be produced which is processed electronically, enabling the defective container to be rejected.

6 Claims, 7 Drawing Figures

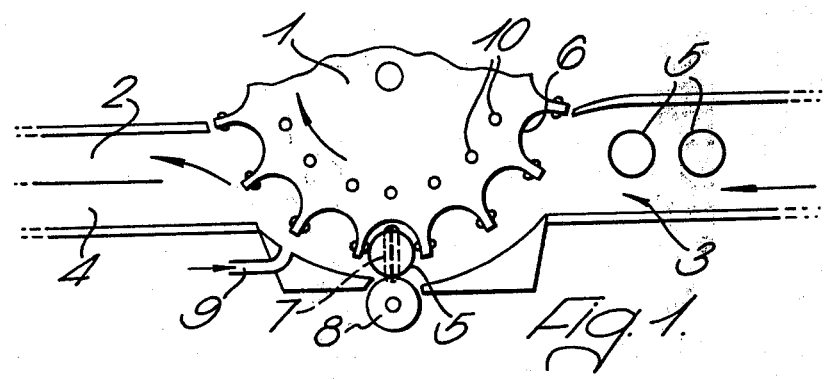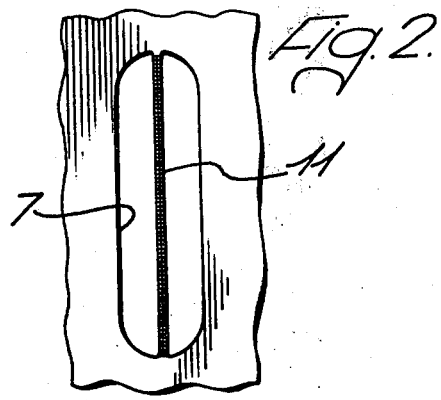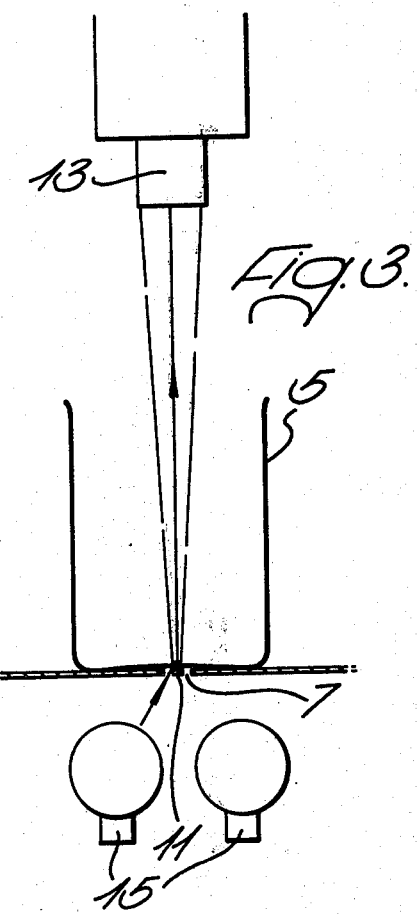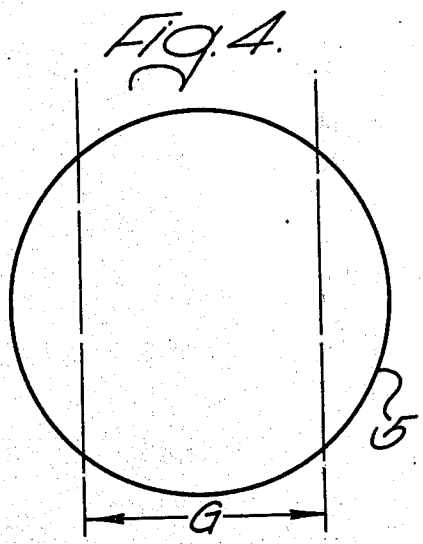

APPARATUS FOR DETECTING THE PRESENCE OF SURFACE IRREGULARITIES IN ARTICLES MADE OF TRANSPARENT MATERIAL

The present invention relates to apparatus for detecting the presence of surface irregularities, especially spikes on the inside base of containers, in articles made of transparent material.

It is very important to detect the presence of such irregularities in articles before the articles leave the factory as they can in certain circumstances be very dangerous to the consumer. "Spikes" in glass containers usually take the form of small, often truncated, cones which stand proud of the surface.

The present invention is concerned with the detection of irregularities of this kind and it is thus an object of the invention to provide an improved method and apparatus for the detection of surface irregularities.

According to the invention, there is provided an apparatus for detecting the presence of surface irregularities in articles made from transparent material which comprises an opaque object, viewing means adapted to be focussed on said object, a light source means positioned behind said object relative to said viewing means whereby light is refracted to said viewing means in the presence of an irregularity in an article under inspection, and means for transporting articles to be inspected between said viewing means and said opaque object, said opaque object being defined by optical slit means having an opaque line disposed longitudinally of the slit means.

The transport means moves the articles to the detection position of the apparatus and preferably causes relative rotation between the articles and slit.

This mechanism may comprise a conveyor and a star wheel/side wheel combination, the star wheel moving the articles from the conveyor to the detection position. In place of a star wheel/side wheel combination a pair of contra-rotating belts may be employed.

The apparatus may also include means for sorting the articles with defects from the non-defective articles. The sorting means may comprise a solenoid-operated air jet.

Preferably the viewing means comprises a light sensitive apparatus focussed on the object, for example a line-scan diode array camera.

The invention will be described further by way of example, with reference to the accompanying drawings, in which:

FIG. 1 is a schematic top plan view of the apparatus;

FIG. 2 is a schematic top plan view of the light transmitting slit;

FIG. 3 is a cross-section of the apparatus;

FIG. 4 is a top plan view of a container showing the gauging width of the slit.

Figure 5:
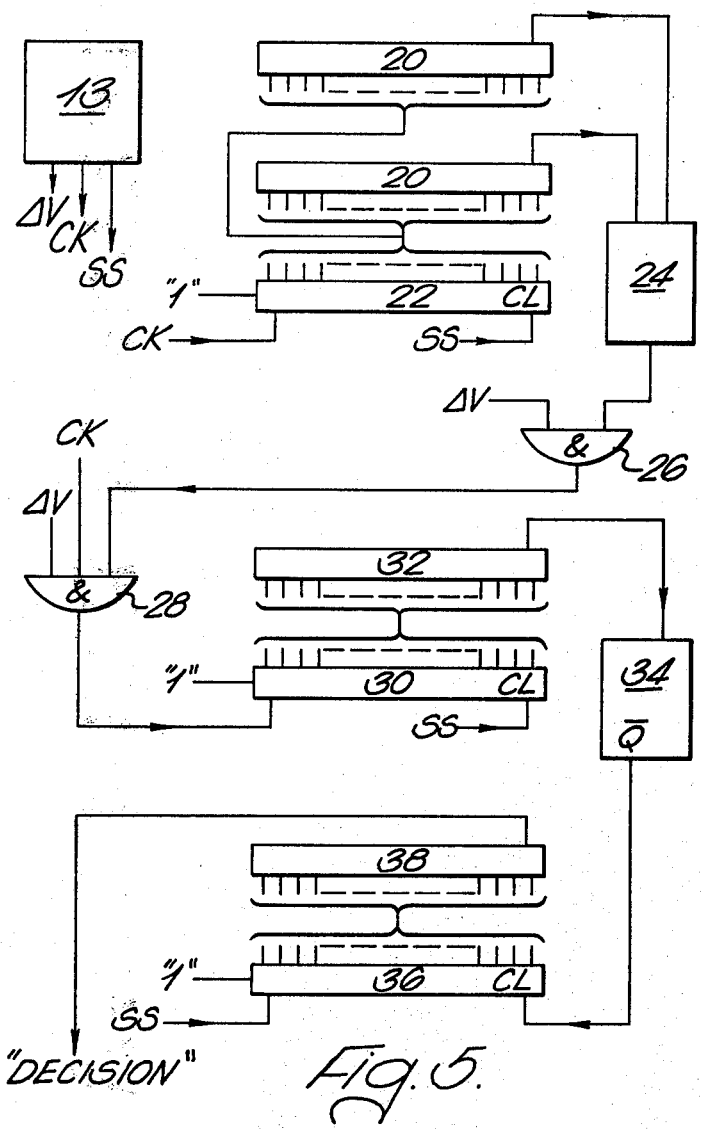
FIGS. 5, 6 and 7 are diagrams of the electronic circuit used in the apparatus.

Referring to FIG. 1, the apparatus comprises a star wheel 1 positioned so that a part of it extends over a conveyor mechanism 3 on which are carried containers 5. A detection slit 7 is disposed at one side of the conveyor mechanism 3 such that it is beneath the periphery of the star wheel 1. An air inlet pipe 9 is positioned to the left of the detection slit 7. The conveyor mechanism to the left-hand side of the star wheel is divided into two sections. Containers with defects pass into section 2 and perfect containers pass into section 4.

A side wheel 8 is positioned adjacent to the detection slit 7 such that when a container is situated over the slit the container is in contact with the side wheel 8. Bolt heads 10 are positioned adjacent to the indentations in the star wheel 1.

FIG. 2 shows the detection slit 7 in greater detail. An opaque line 11 is situated centrally about the longitudinal axis of the slit 7.

FIG. 3 shows a line-scan camera 13 positioned above the container 5 and focussed on the opaque line 11 in the detection slit 7. Beneath the slit 7 are positioned two light bulbs 15.

FIG. 4 shows a typical width of the container 5 which can be tested for defects.

In the embodiment shown in FIG. 1, the conveyor mechanism 3 moves from right to left and the star wheel rotates in a clockwise direction. A container placed on the conveyor mechanism travels into one of the indentations 6 in the star wheel 1 and is transported, by the movement of the star wheel to the detection position so that it covers the detection slit 7 and is beneath the camera 13 which is focussed on the opaque line 11. Light from the light source 15 then passes through the slit 7 and through the base of container 5. The light source 15 can be moved so as to obtain maximum illumination of the slit 7. In the case of the container being in perfect condition, no diffraction of light occurs and hence no light enters the camera since the later views only the opaque line 11. If the base of the container contains defects, light coming through the slit 7 is diffracted so that it travels across the opaque line 11 and hence into the field of view of the camera.

As the containers pass over the slit 7 (at the beginning and end of the passage of each respective container across the slit) there is unwanted diffraction of light into the camera by the sidewalls of the containers 5. This unwanted diffraction is eliminated by imposing a gauging limit on the area of the container which is being scanned for defects. An approximate gauging width G is indicated in FIG. 4.

A proximity detector (not shown) is used to gauge the period during which the container is scanned. The proximity detector comprises a switch activated by the bolt heads 10 on the star wheel 1. To adjust the gauging width, the proximity switch can be moved, thus increasing or decreasing the gauging G width as required.

When a defective container causes a flash of light to enter the camera, a reject signal is triggered in the electronic circuitry and this causes a jet of air to pass through the tube 9. The force of the air pushes the container 3 into section 2 of the left-hand side of the conveyor mechanism. A reject blow is timed to occur from the beginning of the second gauging cycle after detection to the beginning of the third cycle.

When the container 5 is in the detection position covering the slit 7, the container is in contact with the side wheel 8. This side wheel rotates and in doing so rotates the container. The side wheel mechanism is set at a speed for optimum rotation for the required rate of container inspection. A container rotation of at least 90° is needed in order that the whole base area of the container can be scanned due to the imposition of the gauging width. Ideally, there would be a rotation of 360°, as the spikes diffract light differently depending on the angle they make with the light from the light source.

Frequently the containers which have to be inspected have lettering on them. This lettering has a tendency to diffract the light coming from the light source 15 and thus light is seen by the camera. However, the diffraction from the lettering is less intense than that from the spikes and a threshold voltage level within the electronic system allows it to be masked out and thus only diffraction of light from the spikes is recorded.

A number of methods other than the use of a star wheel 1 and side wheel 8 can be employed to rotate the containers. For example contra-rotating belts could be employed. It is also possible to rotate the slit and opaque line 11 across a non-rotating base, but since this requires rotating optics, it is more complicated than the system described.

The electronic circuitry illustrated in FIGS. 5, 6 and 7 will now be described. The camera 13 is a line scan photodiode array camera obtainable commercially from Integrated Photomatrix Ltd of Dorchester, Dorset. The camera 13 includes a linear array of 128 photodiodes which are sequentially scanned at high speed. The camera provides a number of output signals: a start scan pulse signal SS (a pulse being supplied each time a scan of the 128 photodiodes commences), a clock pulse signal CK (synchronous with the scanning of each photodiode), and a video output signal. The video output signal is an analog signal representative of the light intensity received by the scanned (sequentially interrogated) photodiodes. This analog signal is converted to digital form by comparing it to a preset level in a level detector, so providing "on" signals above the level and "off" signals below the level. These on/off signals are termed herein squared video signals $\Delta V$. The level detector is set to provide "off" signals in the absence of refracted light being seen by the camera. An "on" signal thus indicates that the relevant photodiode is viewing refracted light from a spike defect.

In processing the camera outputs to detect validly defects such as spikes, a number of parameters are preset in the electronic circuitry.

Referring to FIG. 2, the field of view for the linear array of 128 photodiodes may be represented as extending along the slit 7 between the numbers 1 and 128. A number of these photodiodes are redundant for defect detecting since only those within the slit area need be employed (the field of view of the camera extends longitudinally further than the end boundaries of the slit. A first parameter which is chosen in the electronic circuitry is the uppermost and lowermost (in number) out of the 128 possible photodiodes which are to be employed.

A second parameter which is present is the number of adjacent (i.e. consecutive) photodiodes in the window which, in any one scan, must sense a high light intensity ($\Delta V$/high) to satisfy the criterion that a true spike defect has been seen. For example, a minor blemish on the container base may cause a light spot on, say, one or two photodiodes which one would not wish determined as a spike defect. Thus, one selects the minimum number of photodiodes selected from those within the window which must have $\Delta V$ high before actuating a "defect present" signal. This parameter essentially sets the distance along the slit for which $\Delta V$ must be high to actuate the "defect present" signal.

A third preset parameter is the number of consecutive scans of the photodiode array for which the "defect present" signal must exist. The parameter is also a means of avoiding minor blemishes being sensed as stippling marks and essentially sets the minimum time for which $\Delta V$ must be high within the window before being decoded as a defect.

The electronic circuitry employed to process the outputs of the camera 13 is illustrated in FIG. 5, where only the more important components are illustrated for clarity. A pair of thumbwheel stores 20 are preset with the sequence number of the lowermost and uppermost diodes in the array of 128 which are to be employed for defect detection. This is the first parameter described above and, in the example given, setting numbers 10 and 100 in the thumbwheel stores will ensure that diodes only from 10 to 100 are employed for defect detection.

A continuous series of "1"s are clocked by the CK signal from camera 13 through a shift register 22 and the latter is cleared by the SS signal from camera 13. The states of the shift register stages are compared to the numbers held by thumbwheel stores 20, and a pulse output is provided at 24 which commences at the lowermost diode number preset (10 in our example) and terminates at the uppermost number preset (100 in our example).

The pulse from 24 is supplied to an AND gate 26, a second input of which receives a $\Delta V$ signal from camera 13. AND Gate 26 is connected to a second AND gate 28 which has $\Delta V$ and CK inputs at two other terminals. The output of AND gate 28 is employed to clock a shift register 30 which has a continuous series of "1"s clocked therethrough. Shift register 20 is cleared by SS signals from camera 13 and the output stages are each compared to a preset number held in a thumbwheel store 32. This latter store is preset with the second parameter described above—the number of consecutive diodes which sense a high light intensity in any one scan before a "defect present" signal is actuated. The comparison output is stored in a flip-flop 34, which is in the "1" state if the preset number of diodes in any one scan is achieved, but which is otherwise in the "0" state.

A further shift register 36 has a continuous series of "1"s clocked through by the SS signals from camera 13 and is cleared by the $\overline{Q}$ output of flip-flop 34. The output stages of shift register 36 are compared to a number preset in a thumbwheel store 38. This latter store is preset with the third parameter described above—the number of consecutive scans for which a "defect present" signal must exist before it is considered to be a true defect. When a "defect present" signal is set by flip-flop 34 ($\overline{Q}=0$), shift register 36 advances a "1" for each scan and if this occurs for a sufficient number of scans corresponding to the number preset in thumbwheel store 38 then an output signal is generated which is termed herein the "Decision" signal. The latter is high when the preset number of photodiodes within the window W have $\Delta V$ high for the preset number of scans; otherwise it is low. A high "Decision" signal indicates that a spike defect has been detected by the camera 13.

Figure 6:
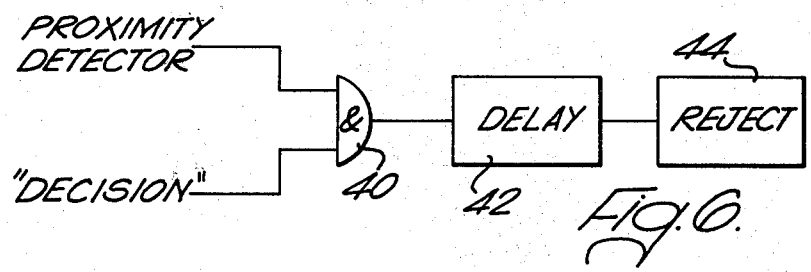
Figure 7:
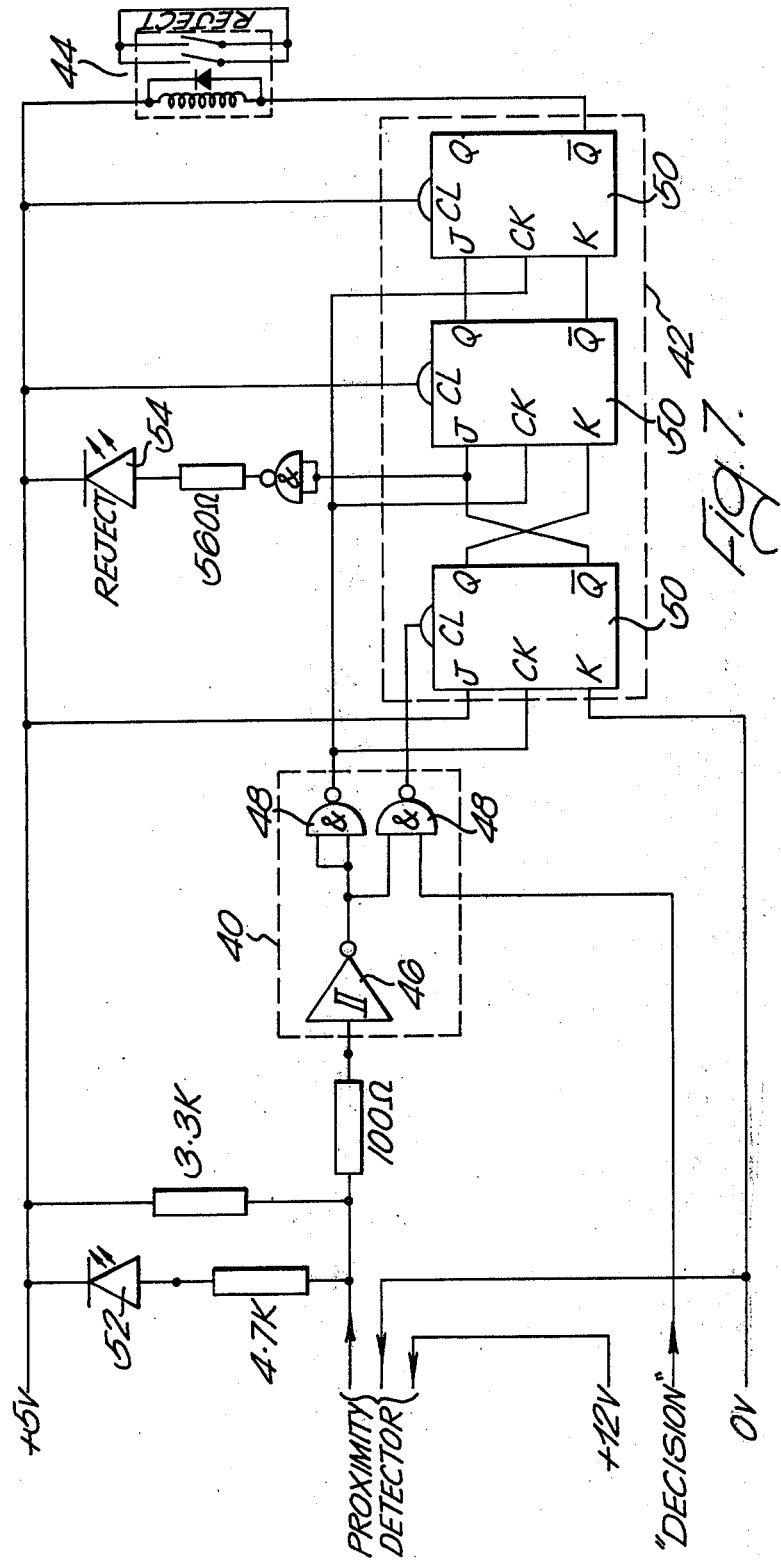

The "Decision" signal can be processed in a number of different ways, but a typical general approach is illustrated in FIG. 6, and a specific example is illustrated in FIG. 7.

Referring to FIG. 6, the "Decision" signal is supplied as one input to an AND gate 40, a second input of which is supplied from the proximity detector which provides the gauging limits during which each container is inspected. The output of AND gate 40 triggers a delay circuit 42 which in turn actuates a reject mechanism 44.

In the presence of a high "Decision" signal during the gauging period, AND gate 40 is enabled, thus triggering delay 42 and causing the container, after the appropriate delay to enable it to clear the inspection station, to be rejected as faulty.

A more detailed embodiment of the FIG. 6 circuitry is shown in FIG. 7, where AND gate 40 comprises an inverter 46 and a pair of NAND gates 48, and the delay circuit 42 comprises 3 JK flip-flops 50. The circuit also includes gauging and reject LED's 52 and 54 respectively providing a visual indication of when gauging is proceeding and when a reject occurs.

The opaque line 11 is shown in FIG. 2 as straight-sided and parallel to the longitudinal axis of slit 7. This configuration is normal for containers with flat bases, but with containers with contoured bases it will be desirable to form the opaque line 11 as a non-straight-sided shape. With containers whose base rises towards the centre (e.g. as in some glass wine bottles) the opaque line 11 is preferably thicker at its centre than at its edges. The shape of the line should be selected so as to provide, at camera 13, a straight line shadow. We have found that with bottles with contoured bases, the correct shape of opaque line is best determined empirically.

We claim:

1. An apparatus for detecting the presence of surface irregularities in the bases of transparent glass containers, which comprises an opaque object, viewing means adapted to be focussed on said object, a light source means positioned behind said object relative to said viewing means whereby light is refracted to said viewing means in the presence of an irregularity in a container under inspection, and means for transporting containers to be inspected between said viewing means and said opaque object, said opaque object being defined by optical slit means having an opaque line disposed longitudinally of the slit means and disposed between the sides of the slit means and said transporting means comprising means for transporting transparent containers across said slit with the container bases adjacent said slit and for causing relative rotation of said containers and slit.

2. An apparatus according to claim 1 wherein said light source means comprises a pair of light sources arranged obliquely of said opaque line with respect to said viewing means.

3. An apparatus according to claim 1 or 2 wherein said viewing means comprises a light-sensitive means.

4. An apparatus according to claim 3 wherein said viewing means comprises means for scanning the opaque line longitudinally.

5. An apparatus according to claim 4 wherein the scanning means comprises a line scan diode array camera.

6. Apparatus for detecting the presence of surface irregularities in the bases of transparent glass containers comprising a light source; a light detector; means intermediate the light source and the light detector for forming an elongated slit of a length approximating the diameter of the containers to be tested, the slit having an opaque line disposed longitudinally within the slit, the arrangement of the source, slit and detector being such that the opaque line prevents light passing through the slit from reaching the detector; and means for transporting glass containers to be inspected between the detector and the slit in such a manner that light passing through the slit passes through the bottom wall of the containers, said transport means also being capable of effecting relative rotation between the containers and the slit.

* * * * *